(12) United States Patent
Lentini et al.

(10) Patent No.: US 6,294,156 B1
(45) Date of Patent: Sep. 25, 2001

(54) COMPOSITIONS WITH ENHANCED PHOTOPROTECTIVE EFFECT AND METHOD FOR USING SAME

(75) Inventors: Peter J. Lentini, Bayside; Rosa M Dwyer, Bay Shore, both of NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/458,632

(22) Filed: Dec. 10, 1999

Related U.S. Application Data

(60) Provisional application No. 60/111,775, filed on Dec. 10, 1998.
(51) Int. Cl.⁷ .............................. A61K 7/42; A61K 7/44; A61K 7/00
(52) U.S. Cl. ............................ 424/59; 424/60; 424/400; 424/401
(58) Field of Search .............................. 424/59, 60, 400, 424/401

(56) References Cited

U.S. PATENT DOCUMENTS

| | | |
|---|---|---|
| 4,052,278 | 10/1977 | Brown et al. . |
| 5,468,471 | 11/1995 | Zecchino et al. . |
| 5,573,754 | 11/1996 | Kulkarni et al. . |
| 5,607,979 | 3/1997 | McCreery . |
| 5,622,690 | 4/1997 | Potter et al. . |
| 5,827,507 | 10/1998 | Oshima et al. . |
| 5,849,316 | 12/1998 | Mellul et al. . |

FOREIGN PATENT DOCUMENTS

| | | |
|---|---|---|
| 704 205 | 4/1996 | (EP) . |
| 05-339139 | 12/1993 | (JP) . |
| 06-135820 | 5/1994 | (JP) . |
| 09 263523 | 10/1997 | (JP) . |
| WO 98/46200 | 10/1998 | (WO) . |

OTHER PUBLICATIONS

International Search Report PCT/US99/29259 (2 pgs.).

*Primary Examiner*—Shelley A. Dodson
(74) *Attorney, Agent, or Firm*—Kenyon & Kenyon

(57) ABSTRACT

The present invention relates to a sunscreen composition for topical application to the skin comprising a fluororesin having a submicron in combination with a sunscreen agent and an oil component. These compositions provide a boost in the SPF value of the composition. The invention also provides methods relating to the use of these compositions for boosting the SPF and decreasing the irritation on the skin caused by irritating sunscreen agents.

23 Claims, No Drawings

COMPOSITIONS WITH ENHANCED PHOTOPROTECTIVE EFFECT AND METHOD FOR USING SAME

This application claims the benefit of provisional No. 60/111,775 filed Dec. 10, 1998.

FIELD OF THE INVENTION

The present invention relates to topically applied sunscreen compositions. In particular, the invention relates to sunscreen compositions containing sunscreen agents that provide an enhanced amount of photoprotection by means of being in combination with submicron fluororesin particles. The sunscreen compositions feel better on the skin and are less irritating than typical sunscreens because the enhanced photoprotection is not achieved by using greater quantities of the sunscreen agent.

BACKGROUND OF THE INVENTION

Sunscreen compositions are frequently used to protect skin that is exposed to the sun for a variety of reasons such as sun bathing, or spending leisure time or working out of doors. Topical sunscreen compositions, which are easily applied to the skin, are usually in the form of a lotion, oil, cream or emulsion (water-in-oil and oil-in-water). Sunscreen compositions contain sunscreen agents to protect the skin from the harmful UV rays of the sun. These rays are generally in the form of UV-A and UV-B radiation which range from about 290 to 400 nm in wavelength.

There are short and long term hazards associated with prolonged exposure to UV radiation. Some of the long term effects include malignant changes in the skin surface, premature aging of the skin as evidenced by wrinkles, yellowing, cracking, telangiectasis (spider vessels), solar keratoses (growths), ecchymoses (subcutaneous hemorrhagic lesions), and loss of elasticity (sagging). A major short term effect of prolonged exposure to UV light is erythema, commonly known as a sunburn.

The amount of photoprotection against erythema is the basis for the determination of the SPF ("sun protection factor") value. The SPF value measures the amount of protection from the sun provided before a certain level of erythema is experienced. Compositions having higher SPF values are preferred because they offer more protection against the harmful effects caused by the sun and UV radiation.

Sunscreen agents act by absorbing, scattering or blocking UV radiation and thus, prevent UV radiation from penetrating the skin. They are available as both organic and inorganic agents. Typical organic agents include. for example. PABAs (p-aminobenzoic acids), benzophenones. salicylate esters and dioxybenzone. Examples of inorganic agents include zinc oxide, titanium dioxide and calamine. To achieve higher SPF values, typically, greater quantities of the sunscreen agent or combination of sunscreen agents are added to the composition. However, greater quantities of sunscreen agents present certain challenges in formulation, especially with respect to stability. For example, titanium dioxide tends to agglomerate and become less effective as a sunscreen agent. It is also a frequent complaint that sunscreens containing particularly high concentrations of titanium dioxide have an unpleasant or grimy feel on the skin and result in a white or blue hue on the skin. Other negative qualities that result from using high concentrations of inorganic sunscreen agents are the opaqueness of the formula when a clear formula is desired. the change in color of the formula, or other adverse aesthetic effects.

Producing a topical sunscreen composition with a high SPF is difficult to achieve without the negative characteristics associated with using larger quantities of sunscreen agents. Efforts to "boost" the SPF value of a sunscreen composition are demonstrated in U.S. Pat. Nos. 5,468,471 and 5,573,754. However, they include components in addition to the sunscreen agent that are relatively costly and not easily manufactured. Thus, there is a continued effort to find ways of boosting the SPF of topical sunscreen compositions. It is, therefore, an object of the present invention to reduce the irritation potential of topical sunscreen compositions to levels which will be acceptable to the average user of the product and to provide a topical sunscreen composition that is appealing to the consumer.

SUMMARY OF THE INVENTION

The present invention relates to a sunscreen composition that has a photoprotective effect enhanced by the combination of a fluororesin polymer of a submicron particle size and a sunscreen agent in a hydrophobic vehicle. The composition enhances the photoprotective effect of the composition without causing adverse skin reactions or being aesthetically unpleasant to the user. An enhancement of the photoprotective effect can be demonstrated, for example, by an increase in SPF by 2 or 3 units. The increase is achieved primarily without adding larger quantities of the sunscreen agent. The invention also relates to a cosmetic or pharmaceutical composition comprising the combination, as well as a method of boosting the SPF value of a sunscreen and methods for reducing the irritancy experienced on the skin and providing photoprotection to the skin by applying to the skin the compositions of the present invention.

The invention is particularly usefull in the preparation of formulations containing octyl methoxycinnamate and benzophenone as well as other organic sunscreen agents because the SPF is increased without adding larger quantities of these organic sunscreen agents or other inorganic sunscreens. Therefore, the stability and aesthetic challenges experienced with larger quantities of organic and inorganic sunscreen agents can be avoided. The compositions and methods of the present invention feel comfortable on the skin, look more appealing and achieve an increased SPF value.

DETAILED DESCRIPTION OF THE INVENTION

It has now been unexpectedly discovered that the SPF value of a sunscreen composition can be increased when a fluororesin polymer having a submicron particle size is combined with a sunscreen agent. The fluororesin polymer of the present invention has been previously used in cosmetic products as described in Japanese Publication Nos. 06-135820, 05-163114, 02-088512, and U.S. Pat. No. 5,093,110, the contents of which are herein incorporated by reference. Fluororesins have been previously described for use in sunscreen compositions. as for example, in Japanese Application Disclosure Nos. 60-149515, 05-339139. However, the use of fluororesins in sunscreens has been in an arrangement where the sunscreen agent surrounds the fluororesin (i.e., the fluororesin is "coated" by the sunscreen) or is bonded to the fluororesin by a chemical reaction. In the present invention the advantages of combining the sunscreen agent with the submicron fluororesin in a composition are described and found to surprisingly boost SPF and reduce irritation on the skin. These benefits and characteristics have not previously been disclosed.

It has been discovered that a certain particle size range of known fluororesins are capable of enhancing the SPF of sunscreen agents. The submicron size of the fluororesin particles effects the ability of fluororesin to achieve, when combined with the sunscreen agent, a boost in the SPF value of the sunscreen composition. The particle size ranges from about 200 nm to about 1200 nm. preferably between about 400 to about 800 nm, and more preferably about 600 nm. The fluororesin can be made by any method known in the art. Methodology for production of submicron fluororesin, for example, is disclosed in U.S. Pat. No. 4,052,278, the contents of which are incorporated herein by reference. While not wishing to be bound by any particular theory, it is believed that the efficacy of these sunscreen compositions in substantially increasing the SPF value of the composition is related to the optical properties of the submicron sized fluororesin particles, which synergistically along with the sunscreen agent prevent the harmful rays of the sun from damaging the skin.

The fluororesins can be any fluorinated polymer which is well known for having low friction properties and for being used as a dry lubricant powder. Preferably, the fluororesin is polytetrafluorethylene ("PTFE"), commonly known as Teflon and available from E.I. Du Pont de Nemours and Company. The fluororesin is a polymer and has a degree of polymerization greater than 20,000. In particular. PTFE is non-sticky and very inert chemically. Therefore, the submicron PTFE particles of the present invention do not react with the other components of the sunscreen composition, but rather, synergistically coexist with the other components. The PTFE is present in the composition in an amount of about 0.1 to about 10.0 percent of the weight of the composition, preferably 0.2 to about 5.0 percent, and more preferably about 0.5 to about 1.0.

The fluororesin is incorporated into an oil component of the final composition. The oil component can be any cosmetically or pharmaceutically acceptable vehicle that is hydrophobic (i.e., oil based). The oil component of the present composition can, in general, include other types of materials that are cosmetically or pharmaceutically acceptable and which are substantially insoluble in water. The materials may be, for example, organic esters or volatile or non-volatile oils. For example, suitable volatile oils include, but are not limited to, both cyclic and linear silicones. such as cyclomethicone, octamethylcyclotetrasiloxane, and decamethylcyclopentasiloxane, or a mixture thereof. Non-volatile oils include, but are not limited to, vegetable oils, such as coconut oil, jojoba oil, corn oil, sunflower oil, palm oil, soybean oil; non-volatile silicones, such as dimethicone, dimethiconol, dimethicone copolyol, phenyl trimethicone, methicone, simethicone; organic esters such as carboxylic acid esters and glyceryl esters. For example, carboxylic acid esters can include isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; and glyceryl esters can include glyceryl stearate, glyceryl dioleate, glyceryl distearate, glyceryl linoleate, glyceryl myristate.

Alternatively, the fluororesin can be pre-dispersed in a hydrocarbon oil and, preferably, in polyisobutene. The hydrocarbon oil may be any hydrocarbon that exists as a liquid at room temperature and has a relatively low viscosity. Therefore, the hydrocarbon oil may be volatile or non-volatile, or a mixture of both. Examples include, but are not limited to, straight or branched chain hydrocarbons having from 1–10 carbon atoms, and other polyalphaolefins such as polydecene, isobutene. Non-volatile hydrocarbons include, for example, mineral oil, liquid paraffins, C2 to C8 paraffins, isoparaffins, squalane, squalene or petrolatum.

The fluororesin can be used to enhance the photoprotective effect of virtually any sunscreen agent to be applied topically. Accordingly, the sunscreen agent can be a wide variety of conventional sunscreen agents, including both organic and inorganic sunscreen agents. Other suitable sun-screening agents include for example, p-aminobenzoic acid, its salts and its derivatives, anthrilates, salicylates, water soluble sunscreens such as Eusolex 232, oil soluble sunscreens, such as octyl methoxycinnamate and other cinnamic acid derivatives, dihydroxycinnamic acid derivatives, trihydroxycinnamic acid derivatives, paramethoxyethylhexyl ester cinnamate, hydrocarbons such as diphenylbutadiene, stilbene, particulate sunscreens such as zinc oxide and titanium dioxide, dibenzalacetone and benzalacetophenone, naphtholsulfonates, dihydroxynaphthoic acid and its salts, o- and p-hydroxybiphenyldisulfonates, coumarin derivatives, diazoles, quinine slats, quinoline derivatives, benzophenones or hydroxy- or methoxy- substituted benzophenones, benzophenone carbonate, uric and vilouric acids, tannic acid and its derivatives, hydroquinone, 4-isopropyldibenzoylmethane, butylmethoxydibenzoyl-methane, etocrylene, octocrylene, 2-ethylhexysalicylate, glyderyl p-aminobenzoate, 3,3,5-trimethylcyclohexysalicylate, methylanthranilate, menthyl anthranilate, p-dimethyl-aminobenzoic acid or aminobenzoate, 2-ethylhexyl p-dimethylamino-benzoate, 2-phenyl-benzimidazole-5-sulfonic acid, 2-(p-dimethylaminophenyl)-5-sulfonicbenzoxazoic acid and mixtures of these compounds.

In a particularly preferred embodiment, the sunscreen agent is an organic sunscreen such as octyl methoxycinnamate or benzophenone. More preferably, the organic sunscreen is octyl methoxycinnamate. The amounts will vary depending on the sunscreen that is chosen and the desired SPF. Preferably, the amount of organic sunscreen is from about 1 to about 10 percent of the weight of the composition. SPF is a value which measures the amount of photoprotection against erythema that a sunscreen provides. The number is based on the minimal erythemal dose ("MED"), the least exposure dose at a specific wavelength that will elicit a delayed response in erythema. The MED is an indicator of how much energy reaches the skin and the responsiveness of the skin to the radiation to which it is subjected. The SPF value is calculated by dividing the MED of protected skin by the MED of unprotected skin.

In particular, the present invention provides sunscreen compositions of varying SPF values. Typical sunscreens wyhich have an SPE value in the range of about 15 to about 25 are formulated to contain about 8 to 12 percent of titanium dioxide to achieve an SPF of about 25 and about 5 to 6 percent to achieve an SPF of about 15 in addition to other inorganic sunscreen agents. In contrast, according to the present invention a sunscreen formulation of about 25 SPF contains about 1 to 2 percent titanium dioxide in addition to other inorganic sunscreen agents, a reduction of about 25 percent. Accordingly, in the present invention, the sunscreen agent is present in an amount of from about 1 to about 20 percent by weight of the total composition. Preferably. the sunscreen agent is about 3 to about 10 percent.

Another advantage of combining the submicron fluororesin with sunscreen agents is the ability to reduce the amount of irritation experienced with the use of sunscreens. The irritation caused by excessive amounts of sunscreen agents used is commonly known in the art. By being able to reduce the amount of sunscreen agent and in particular the inorganic sunscreen agent, titanium dioxide, and the organic sunscreen agent, octyl methoxycinnamate, the amount of irritation is reduced.

The compositions of the present invention may also comprise other optional components, depending on the intended end use. These include, but are not limited to, oil soluble colorants (such as D&C Green #6); antioxidants (such as BHT); chelating agents (such as disodium EDTA); dispersion stabilizers or thickeners such as clay, silica, fluorinated surfactants, and other general surfactants, preservatives (such as methyl paraben), fragrances (such as pinene); flavoring agents (such as sorbitol); humectants (such as glycerine); waterproofing agents (such as PVP/ eicosene copolymer); oil-soluble film formers (such as hydrogenated C-9 resin); cationic polymers (such as polyquaternium 10); anionic polymers (such as xanthan gum); vitamins (such as tocopherol); and the like.

The benefit of combining the submicron fluororesin with a sunscreen agent is obtained in any type of a water-in-oil or oil-in-water emulsion, or anhydrous composition. The compositions of the present invention can be used in any type of makeup or in any type of skin or sun care product. Typical examples include foundations, eyeshadows, eyeliners, mascaras, blushes, powders, lipsticks, lipglosses, lip paints, oil control skin mattifiers, and sunscreen lotions. The present invention further comprises pharmaceutically or cosmetically acceptable sunscreen carrier materials selected as appropriate for the form and aesthetic characteristics desired for the composition being formulated. Suitable carrier materials useful for sunscreen compositions as described herein are well known in the art, and their selection is readily made by one of ordinary skill in the art.

The present invention also relates to methods for providing photoprotection to the skin. The methods comprise topically applying to the skin a safe and photoprotectively effective amount of the compositions according to the present invention. In addition, the fluororesin sunscreen compositions of the present invention can be used to completely eliminate the use of inorganic sunscreens. The sunscreen compositions can be used in categories other than cosmetic or pharmaceutical, for example, the compositions of the present invention can be used in paints and coatings applied to surfaces.

The invention is further illustrated by the following non-limiting examples.

EXAMPLE I

A composition, having an SPF of about 15, according to the present invention is prepared as follows:

| Material | Weight % |
|---|---|
| Phase I | |
| Purified Water | 35.0 |
| Alkoxylated Alcohol | 1.8 |
| Butylene Glycol | 4.5 |
| Phenoxyethanol | 1.0 |
| Disodium EDTA | 0.2 |
| Sodium Chloride | 0.8 |
| Sucrose | 2.0 |
| Phase II | |
| Octyl Methoxycinnamate | 8.0 |

-continued

| Material | Weight % |
|---|---|
| Cyclomethicone | 7.0 |
| BHT | 0.3 |
| Linoleic Acid | 0.4 |
| Bishydroxyethyl Biscetyl Malonamide | 0.4 |
| Alkyl Benzoate | 7.0 |
| Dimethicone | 4.0 |
| PEG-30 Dipolyhydroxystearate | 1.0 |
| Phase III | |
| PTFE | 2.8 |
| Polyisobutene | 11.0 |
| Phase IV | |
| Cetyl Dimethicone Copolyol | 8.0 |
| Cyclomethicone | 4.8 |
| Tocopheryl Acetate | 0.5 |

To prepare the composition, Phase I and II materials are combined by mixing with a homogenizer at 3600 rpm; this mixture is then heated to 70° C. and mixed for about five minutes. After homogenization, the emulsion is allowed to cool. Phase III materials, including the PTFE provided by Shamrock Technologies Inc., Newark, N.J., are combined with Phase I and II materials by mixing. Finally, the remaining Phase IV materials are added and mixed together.

EXAMPLE II

A composition according to Example I, containing 7.5 percent octyl methoxycinnamate as the sunscreen agent, is studied with and without fluororesin to determine the amount of boost in SPF.

A panel of 5 individuals is selected to participate in the test. The panelists have Fitzpatrick type I-II skin. Particularly, the skin on the backs of the panelists are evenly colored and free of blemishes, stretch marks and discolorations. A standard SPF protocol is followed and uses a Berger Solar Simulator. The MED of the panelists is determined. Two areas are marked on the backs of the panelists. A composition is prepared according to Example I above containing 7.5 percent octyl methoxycinnamate and 2.8 percent fluororesin is applied to one area and a composition containing the same amount of 7.5 percent of octyl methoxycinnamate without fluororesin (i.e., the control) is applied to the second area. Both applications are in an amount of about 2 mg/cm$^2$ and allowed to dry for about 15 to 20 minutes. These areas are exposed to about 10 to 15 times the previously determined MED. The SPF value for formula prepared according to the present invention shows an increase in the SPF.

What we claim is:

1. A sunscreen composition having enhanced photoprotective effect comprising a sunscreen agent in combination with a fluororesin polymer having a submicron particle size.

2. The composition of claim 1 in which said fluororesin has an average particle size of about 200 to about 1200 nm.

3. The composition of claim 2 in which said fluororesin is polytetrafluorethylene.

4. The composition of claim 3 in which said fluororesin is present in an amount of from about 0.1 to about 10.0 percent by weight of the total composition.

5. The composition of claim 1 in which said fluororesin is present in an amount of from about 0.2 to about 5.0% by weight and said sunscreen agent is present in an amount of from about 1 to about 20 percent by weight of the total composition.

6. The composition of claim 1 in which said sunscreen agent is present in an amount of from about 1 to about 20 percent by weight of the total composition.

7. The composition of claim 6 in which said sunscreen agent is organic, inorganic or a combination thereof.

8. The composition of claim 7 in which said sunscreen is organic.

9. The composition of claim 8 in which said sunscreen agent is octyl methoxycinnamate.

10. The composition of claim 7 in which said sunscreen agent is inorganic.

11. The composition of claim 10 in which said sunscreen agent is titanium dioxide.

12. The composition of claim 1 in which said composition further comprises an oil component.

13. The composition of claim 12 in which said oil component is a hydrophobic vehicle.

14. The composition of claim 13 in which said hydrophobic vehicle is a hydrocarbon.

15. The composition of claim 14 in which said hydrocarbon is polyisobutene.

16. The composition of claim 1 which has an SPF from about 15 to about 25.

17. The composition of claim 1 which has an SPF of at least about 15.

18. A cosmetic or pharmaceutical composition comprising from about 0.1 to about 10.0 percent of a fluororesin polymer having a submicron particle size dispersed in a hydrophobic vehicle in combination with a sunscreen agent.

19. A cosmetic or pharmaceutical composition comprising from about 0.1 to about 10.0 percent of a fluroresin polymer having a submicron particle size dispersed in a hydrocarbon vehicle in combination with an organic sunscreen agent.

20. A method of boosting the SPF of a sunscreen composition comprising applving to the skin the composition of claim 1.

21. A method of boosting the SPF of a sunscreen composition comprising applying to the skin the composition of claim 18.

22. A method of boosting the SPF of a sunscreen composition comprising applying to the skin the composition of claim 19.

23. A method of decreasing the irritation on the skin caused by a sunscreen agent comprising applying to the skin the composition of claim 1.

* * * * *